US011959207B2

(12) United States Patent
Peniston et al.

(10) Patent No.: US 11,959,207 B2
(45) Date of Patent: Apr. 16, 2024

(54) POLYMERIC MESH PRODUCTS, METHOD OF MAKING AND USE THEREOF

(75) Inventors: Shawn J. Peniston, Easley, SC (US); Georgios T. Hilas, Anderson, SC (US)

(73) Assignee: Poly-Med, Inc., Anderson, SC (US)

(*) Notice: Subject to any disclaimer, the term of this patent is extended or adjusted under 35 U.S.C. 154(b) by 0 days.

(21) Appl. No.: 13/445,525

(22) Filed: Apr. 12, 2012

(65) Prior Publication Data

US 2013/0267137 A1 Oct. 10, 2013

Related U.S. Application Data

(60) Provisional application No. 61/621,315, filed on Apr. 6, 2012.

(51) Int. Cl.
*D04B 21/12* (2006.01)
*A61F 2/00* (2006.01)

(52) U.S. Cl.
CPC ............ *D04B 21/12* (2013.01); *A61F 2/0063* (2013.01); *A61F 2002/0068* (2013.01); *A61F 2210/0004* (2013.01); *A61F 2250/0031* (2013.01); *D10B 2401/12* (2013.01); *D10B 2509/08* (2013.01); *Y10T 442/184* (2015.04)

(58) Field of Classification Search
CPC .......... A61F 2210/0004; A61F 2/00–28; A61F 2/0063–2002/0072; D04B 21/06–12; D04B 21/20–207
See application file for complete search history.

(56) References Cited

U.S. PATENT DOCUMENTS

| 5,403,347 | A | 4/1995 | Roby et al. |
| 7,875,063 | B1* | 1/2011 | Sander et al. ............... 606/300 |
| 8,128,954 | B2 | 3/2012 | Davis et al. |
| 2002/0161168 | A1 | 10/2002 | Shalaby |
| 2004/0029478 | A1* | 2/2004 | Planck ................ A61F 2/0063 442/318 |
| 2005/0070930 | A1* | 3/2005 | Kammerer .................. 606/151 |
| 2005/0149158 | A1 | 7/2005 | Hunter et al. |
| 2005/0244455 | A1* | 11/2005 | Greenawalt .................. 424/423 |
| 2006/0161160 | A1 | 7/2006 | Sander et al. |
| 2006/0240063 | A9 | 10/2006 | Hunter et al. |

(Continued)

FOREIGN PATENT DOCUMENTS

| CA | 2868750 | 4/2012 |
| CN | 1775188 | 5/2006 |

(Continued)

OTHER PUBLICATIONS

Junge, K., et al., Elasticity of the anterior abdominal wall and impact for reparation of incisional hernias using mesh implants, Hernia, Sep. 2001; 5(3): 113-118 (Abstract).

(Continued)

*Primary Examiner* — Marla D McConnell
*Assistant Examiner* — Kevin Worrell
(74) *Attorney, Agent, or Firm* — Meunier Carlin & Curfman LLC

(57) ABSTRACT

A polymeric mesh is disclosed. The polymeric mesh comprises an absorbable polymeric fiber and a non-absorbable polymeric fiber knitted together to form an interdependent, co-knit mesh structure. Also disclosed are methods for making the polymeric mesh and methods for using the polymeric mesh.

17 Claims, 7 Drawing Sheets

INITIAL

6-WEEKS

(56) References Cited

U.S. PATENT DOCUMENTS

| | | | |
|---|---|---|---|
| 2007/0055093 | A1 | 3/2007 | Beraud |
| 2007/0282160 | A1 | 12/2007 | Sheu et al. |
| 2008/0119848 | A1* | 5/2008 | Shalaby et al. ............... 606/60 |
| 2008/0208325 | A1* | 8/2008 | Helmus et al. ............. 623/1.44 |
| 2008/0208360 | A1 | 8/2008 | Meneghin |
| 2009/0024162 | A1 | 1/2009 | Shalaby |
| 2009/0110713 | A1 | 4/2009 | Lim |
| 2009/0203632 | A1 | 8/2009 | Avelar |
| 2009/0263457 | A1 | 10/2009 | Trollsas et al. |
| 2009/0299408 | A1* | 12/2009 | Schuldt-Hempe et al. .. 606/230 |
| 2009/0326565 | A1* | 12/2009 | Trabucco et al. ............ 606/151 |
| 2010/0016872 | A1* | 1/2010 | Bayon et al. ................ 606/151 |
| 2010/0189763 | A1 | 7/2010 | Nettles |
| 2010/0318108 | A1 | 12/2010 | Datta et al. |
| 2010/0331613 | A1* | 12/2010 | Centonze et al. ............. 600/37 |

FOREIGN PATENT DOCUMENTS

| | | |
|---|---|---|
| CN | 101348972 | 1/2009 |
| CN | 201280073700.2 | 4/2012 |
| EP | 1520552 | 7/2008 |
| EP | 2016956 | 1/2009 |
| EP | 1771124 | 12/2010 |
| EP | 12873533.9 | 4/2012 |
| EP | 17177458.1 | 4/2012 |
| WO | WO2006111664 | 10/2006 |
| WO | WO2007022201 | 2/2007 |
| WO | WO2011/103141 | 8/2011 |
| WO | PCT/US2012/033336 | 4/2012 |

OTHER PUBLICATIONS

U.S. Appl. No. 13/858,704, filed Apr. 8, 2013, Penniston, S. J.
U.S. Appl. No. 61/621,315, Penniston, S.J.
Azo Materials, "Polyethylene Terephthalate Polyester (PET, PETP)—Properties and Applications"—Supplier data by Goodfellow. Jun. 25, 2003. https://ww.azom.com/article.aspx?ArticleID=2047 (Year:2003).
NonFinal Office Action, dated May 8, 2014 in U.S. Appl. No. 13/858,705, inventor-Penniston, et al., 10 pgs.
Response to Nonfinal Office Action, dated Sep. 10, 2014, in U.S. Appl. No. 13/858,705, inventor-Penniston, et al., 10 pgs.
Final Office Action, dated Dec. 31, 2014, in U.S. Appl. No. 13/858,705, inventor-Penniston, et al., 11 pgs.
Amendment after Final and Advisory Action, dated Jun. 11, 2015, in U.S. Appl. No. 13/858,705, inventor-Penniston, et al., 15 pgs.
Request for Continued Examination, dated Jun. 24, 2015, in U.S. Appl. No. 13/858,705, inventor-Penniston, et al., 3 pgs.
Nonfinal Office Action, dated Dec. 4, 2015, in U.S. Appl. No. 13/858,705, inventor-Penniston, et al., 11 pgs.
Response to Nonfinal Office Action, dated May 23, 2016, in U.S. Appl. No. 13/858,705, inventor-Penniston, et al., 11 pgs.
Final Office Action, dated 0-23-2016, in U.S. Appl. No. 13/858,705, inventor-Penniston, et al., 10 pgs.
Response to Final Office Action and RCE, dated Feb. 23, 2017, in U.S. Appl. No. 13/858,705, inventor-Penniston, et al., 10 pgs.
NonFinal Office Action, dated Jul. 3, 2017, in U.S. Appl. No. 13/858,705, inventordated-Penniston, et al., 11 pgs.
Response to NonFinal Office Action, dated Jan. 3, 2018, in U.S. Appl. No. 13/858,705, inventor-Penniston, et al., 9 pgs.
International Preliminary Report on Patentability, dated Oct. 7, 2015, in PCT/US2012/033336, inventor-Penniston, et al., 8 pgs.
International Search Report, dated Dec. 30, 2013, in PCT/US2012/033336, inventor-Penniston, et al., 4 pgs.
Decision to Grant, dated Jun. 1, 2017, in European Patent Application No. 12873533.9, inventor-Penniston, et al., 1 pg.
Communication under Rule 71(3) EPC, dated Feb. 20, 2017, in European Patent Application No. 12873533.9, inventor-Penniston, et al., 8 pages.
Communication under Rule 94(3), dated Jul. 8, 2016, Feb. 20, 2017, in European Patent Application No. 12873533.9, inventor-Penniston, et al., 5 pages.
European Search Report, dated Nov. 4, 2015, in European Patent Application No. 12873533.9, inventor-Penniston, et al., 7 pages.
Canadian Office Action, dated Jan. 18, 2018, in Canadian Patent Application No. 2,868,750, inventor-Penniston, et al., 4 pgs.
European Search Report, dated Aug. 11, 2017, in European Patent Application No. 17177458.1, inventor-Penniston, et al., 8 pgs.
First Office Action, dated Jul. 27, 2015, in Chinese Patent Application No. 201280073700.2, inventor-Penniston et al., 15 pgs.
Second Office Action, dated May 18, 2016, in Chinese Patent Application No. 201280073700.2, inventor-Penniston et al., 10 pgs.
Rejection Decision, dated Nov. 23, 2016, in Chinese Patent Application No. 201280073700.2, inventor-Penniston et al., 9 pgs.
Reexamination Notice, dated Mar. 23, 2018, in Chinese Patent Application No. 201280073700.2, inventor-Penniston et al., 8 pgs.
Final Office Action, dated May 18, 2018, for U.S. Appl. No. 13/858,704 (11 pgs).
Response to Final Office Action, dated Jul. 18, 2018, for U.S. Appl. No. 13/858,704 (11 pgs).
Supplemental Response to Final Office Action, dated Aug. 7, 2018, for U.S. Appl. No. 13/858,704 (10 pgs).
Second Supplemental Response to Final Office Action, dated Aug. 21, 2018, for U.S. Appl. No. 13/858,704 (14 pgs).
NonFinal Office Action, dated Oct. 2, 2020, for U.S. Appl. No. 13/858,704 (12 pgs).
Response to NonFinal Office Action, dated Feb. 3, 2021, for U.S. Appl. No. 13/858,704 (17 pgs).
NonFinal Office Action, dated May 31, 2019, for U.S. Appl. No. 13/858,704 (10 pgs).
Response to NonFinal Office Action, dated Sep. 3, 2019, for U.S. Appl. No. 13/858,704 (8 pgs).
Final Office Action, dated Nov. 29, 2019, for U.S. Appl. No. 13/858,704 (10 pgs).
Response to Final Office Action, dated Apr. 29, 2020, for U.S. Appl. No. 13/858,704 (17 pgs).
Response to NonFinal Office Action, dated Feb. 3, 2021, for U.S. Appl. No. 13/858,704 (10 pgs).
Final Office Action, dated May 4, 2021, for U.S. Appl. No. 13/858,704 (10 pgs).
Response to Final Office Action, dated Aug. 10, 2021, for U.S. Appl. No. 13/858,704 (10 pgs).
NonFinal Office Action, dated Oct. 29, 2021, for U.S. Appl. No. 13/858,704 (12 pgs).
Response to NonFinal Office Action, dated Feb. 25, 2022, for U.S. Appl. No. 13/858,704 (10 pgs).
Final Office Action, dated Jun. 10, 2022, for U.S. Appl. No. 13/858,704 (13 pgs0.
Response to Final Office Action, dated Oct. 10, 2022, for U.S. Appl. No. 13/858,704 (13 pgs).
NonFinal Office Action, dated Dec. 21, 2022, for U.S. Appl. No. 13/858,704 (10 pgs).
Office Action, dated Mar. 4, 2020, for European Patent Application No. 17177458 (8 pgs).
Decision to Grant, dated Nov. 26, 2020, for European Patent Application No. 17177458 (1 pgs).
Extended EP Search, dated Dec. 22, 2020, for European Patent Application No. 20216372 (10 pgs).
Office Action, dated Jan. 21, 2022, for Chinese Patent Application No. 202010097834.4 (5 pgs).
Grant, dated Sep. 7, 2022, for Chinese Patent Application No. 202010097834.4 (4 pgs).
Publication Notice, dated Mar. 26, 2021, for Hong Kong Patent Application No. 42020022159.6 (1 pg).
Notice of Allowance, dated Jan. 30, 2020, for Canadian Patent Application, No. 2868750, (1 pg).
Reinstatement, dated Oct. 28, 2019, for Canadian Patent Application, No. 2868750, (1 pg).
Issue Fee Payment, dated May 26, 2020, for Canadian Patent Application, No. 2868750, (2 pgs).

* cited by examiner

INITIAL                6-WEEKS

INITIAL         7-WEEKS

POLYMERIC MESH PRODUCTS, METHOD OF MAKING AND USE THEREOF

This application claims the priority of U.S. Provisional Patent Application No. 61/621,315, filed on Apr. 6, 2012. The entirety of the provisional application is incorporated herein by reference.

FIELD

This application relates generally to polymeric meshes and, in particular, to implantable polymeric meshes having a fast-degrading component and a slow-degrading component.

BACKGROUND

Polymeric meshes have been widely used in medical practice as wound dressing, molded silicone reinforcement, catheter anchoring and pacemaker lead fixation. Implantable polymeric meshes have also been used in surgery for the treatment of hernia, urinary incontinence, vaginal prolapse and other medical conditions. An ideal implantable mesh should be strong, compliant, non-allergenic, sterilizable, chemically inert to the biologic environment, resistant to infection, dimensionally and chemically stable in vivo, non-carcinogenic and cost effective. The mesh should also stimulate fibroblastic activity for optimum incorporation into the tissue with no long-term reaction.

While many polymeric meshes have been developed in recent years, all of them contain some disadvantages. For example, when used for abdominal wall hernia repairs, meshes constructed of fast absorbing polyglycolide-based fiber provide inadequate strength beyond three to four weeks of breaking strength retention, while meshes constructed from relatively slow degrading high-lactide fiber has generated little to no interest. This situation has left the majority of soft tissue repair load bearing applications to be filled by non-absorbable materials, which suffer distinctly from undesirable features associated, in part, with their inability to (1) possess short-term stiffness to facilitate tissue stability during the development of wound strength; (2) gradually transfer the perceived mechanical loads as the wound is building mechanical integrity; and (3) provide compliance with load transfer to the remodeling and maturing mesh/tissue complex. Therefore, there still exists a need for further development of implantable polymeric meshes.

SUMMARY

One aspect of the present invention relates to a polymeric mesh which comprises an absorbable polymeric fiber. For example, the present invention provides a polymeric mesh comprising: an absorbable polymeric fiber comprising from 30% to 60% by weight of the polymeric mesh; a non-absorbable synthetic polymeric fiber, selected from polyethylene with a denier of 60-150 g/9000 m or polypropylene with a denier of 130-180 g/9000 m or mixtures thereof wherein said non-absorbable synthetic fiber has an ultimate elongation of greater than 30%; wherein said absorbable polymeric fiber and said non-absorbable polymeric fiber are knit such that the fibers only partially traverse and partially intersect one another to form an interdependent single layer mesh structure comprising at least two different strength profiles including an early stiff phase and a later extensible phase that results after degradation of the absorbable polymeric fiber; and wherein after degradation of the absorbable polymeric fiber, the remaining non-absorbable fiber forms an interconnected, interlaced, continuous patterned mesh. In addition, the present invention provides a polymeric mesh comprising: an absorbable polymeric fiber; a non-absorbable synthetic polymeric fiber comprising polyethylene with a denier of 60-150 g/9000 m or polypropylene with a denier of 130-180 g/9000 m wherein said non-absorbable synthetic fiber has an ultimate elongation of greater than 30%; wherein said absorbable polymeric fiber and said non-absorbable polymeric fiber are knit such that the fibers only partially traverse and partially intersect one another to form an initially interdependent single layer mesh structure that exhibits at least two different strength profiles including an early stiff phase and a later extensible phase that results after degradation of the absorbable polymeric fiber and subsequent loss of the interdependent mesh structure; and wherein after degradation of the absorbable polymeric fiber, the remaining non-absorbable fiber forms an interconnected, interlaced, continuous patterned mesh.

Another aspect of the present application relates to a polymeric mesh comprising an absorbable polymeric fiber, and a non-absorbable synthetic polymeric fiber, wherein the absorbable polymeric fiber and the non-absorbable polymeric fiber are co-knit to form an interdependent mesh structure. In certain embodiments, the polymeric mesh has long-term force-extensional characteristics that are compatible with surrounding tissues at an implantation site.

Another aspect of the present application relates to a method for producing a polymeric mesh. The method comprises warp knitting an absorbable fiber with a non-absorbable fiber to form an interdependent, co-knit mesh, and heat setting the knit mesh at 80-130° C. for 0.5-1.5 hours. In certain embodiments, the absorbable fiber is knit in a 2 bar marquisette pattern and the non-absorbable fiber is knit in a 2 bar sand-fly net pattern with all guide bars for each pattern threaded 1-in and 1-out.

DETAILED DESCRIPTION

Figure 1:
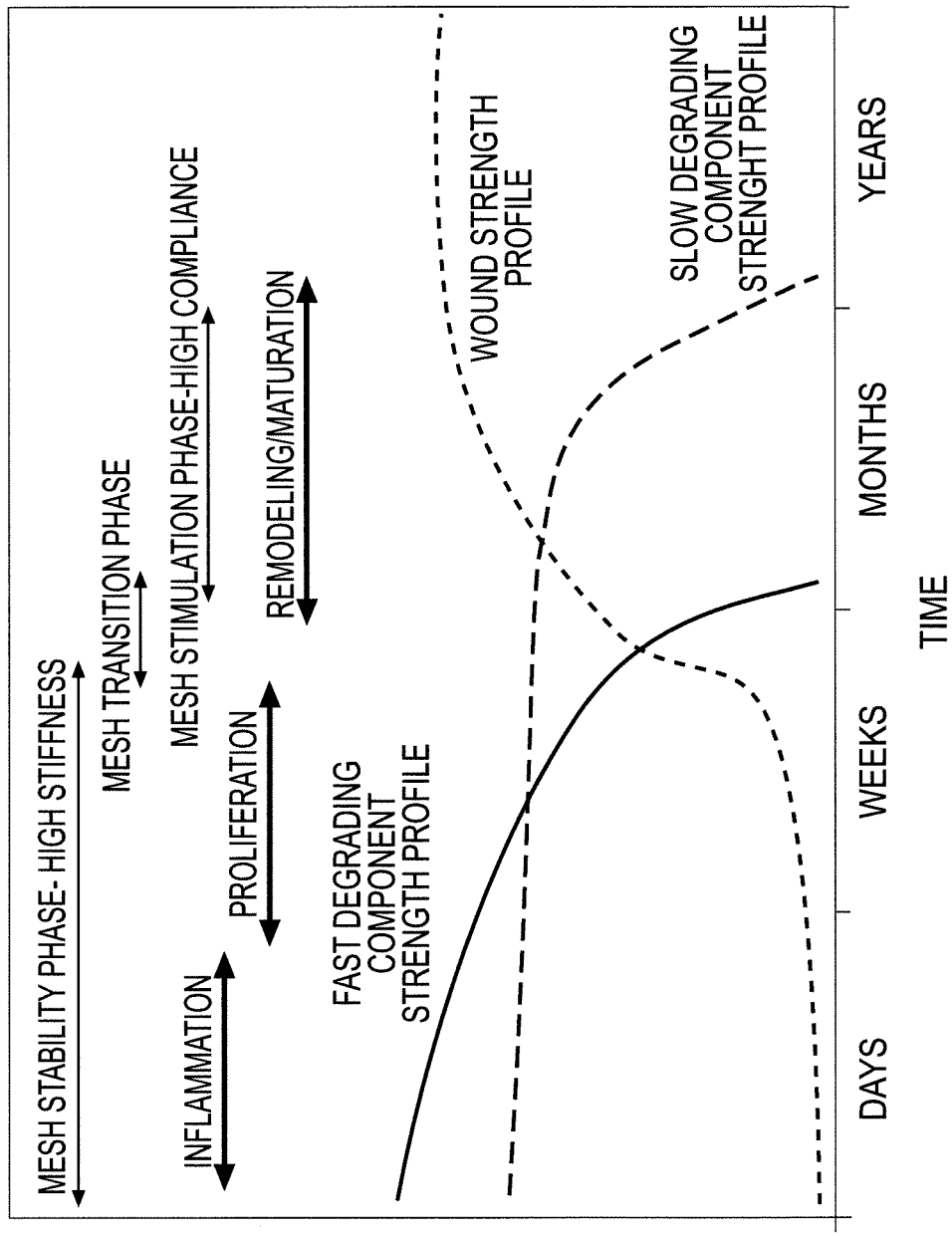
FIG. 1 is a diagram superimposing the modulated mechanical characteristics of a polymeric mesh of the present application with the temporal wound healing process.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention.

In case of conflict, the present specification, including definitions, will control. Following long-standing patent law convention, the terms "a," "an" and "the" mean "one or more" when used in this application, including in the claims.

One aspect of the present application relates to a polymeric single layer multicomponent mesh comprising a fast-degrading component, a slow-degrading component and/or a non-absorbable component. In some embodiments, the polymeric mesh comprises a first mesh formed from a first fiber and a second mesh formed from a second fiber, where the fibers are co-knitted together in an interdependent manner to form an interdependent single layer mesh structure. The first fiber is interlaced with the mesh formed from the second fiber and at least partly traverses the knit pattern of the mesh formed from the second fiber such that the mesh formed by the first fiber restricts uniaxial and multiaxial deformation of the part of the polymeric single layer multicomponent mesh formed by the second fiber. In some embodiments, the absorbable fiber and non-absorbable fiber are co-knit using different knit patterns. In other embodiments, the knit pattern of the non-absorbable fiber facilitates uniaxial and multiaxial deformation subsequent to the substantial loss of mechanical properties for the absorbable fiber knit mesh. The polymeric mesh provides structural stability to developing neotissue at an implantation site.

In some embodiments, the first fiber is an absorbable fiber and the second fiber is a non-absorbable fiber. The absorbable fiber may form an absorbable mesh that is interlaced with a non-absorbable mesh that is formed from the non-absorbable fiber, where absorbable fiber at least partly traverses the knit pattern of the non-absorbable mesh such that the mesh formed from the absorbable fiber restricts uniaxial and multiaxial deformation of the non-absorbable mesh formed from the non-absorbable fiber.

In some embodiments, the first fiber is an absorbable fiber and the second fiber is a non-absorbable fiber.

In other embodiments, both the first and the second fibers are absorbable. The first fiber is a fast-absorbable fiber that constitutes the absorbable component and is substantially degraded over a relative short period of time (e.g., 1-9 months), while the second fiber is a slow-absorbable fiber that constitutes the non-absorbable component and is substantially degraded over a relatively long period time (e.g., 9-60 months).

In certain embodiments, the polymeric mesh comprises more than two different types of fibers. In some embodiments, the polymeric mesh comprises three different types of fibers, e.g., a non-absorbable fiber, a slow-absorbable fiber that is absorbed in 2-12 months after transplantation, and a fast-absorbable fiber that is absorbed within 2 months after transplantation. In other embodiments, the polymeric mesh comprises four different types of fibers. In some other embodiments, the two or more types of fibers are knitted in two or more different types knit patterns. In some embodiments, the polymeric mesh comprises 2, 3, 4 or more different types of fibers knitted in 2, 3, 4 or more different types of knit patterns. In other embodiments, the different types of fibers are not contiguous across the entire mesh, e.g., one section of the mesh is entirely non-absorbable, whereas other sections of the mesh may be slow-absorbable and/or fast-absorbable. In some embodiments, the mesh is dual-, tri- or quad-phased mesh with different regions of composition and absorbability.

The polymeric mesh provides at least two different strength profiles during a wound healing process: an early stiff phase (due to the presence of both the absorbable component and the non-absorbable component) and a later extensible phase (after the degradation of the absorbable component). The early stiffness facilitates uninterrupted tissue integration and angiogenesis, while reducing the risk of recurrence from applied wound stresses prior to the development of wound strength, especially at points of fixation such as those using sutures, tacks, or biocompatible glues. In addition, the added stiffness and stability may resist and/or minimize the wound contraction process. As the wound develops load bearing capability, stress is slowly transferred as the absorbable component degrades and loses strength. Once the absorbable component of the polymeric mesh is removed, the non-absorbable component is well encapsulated in the extracellular matrix. The mesh is positioned in a relaxed configuration such that the newly deposited collagen becomes load bearing and tensional homeostasis is returned to the wounded tissue. Over the ensuing months the remodeling/maturing process of collagen degradation and synthesis adapts the tissue to the loading conditions. In some embodiments, the non-absorbable component of the polymeric mesh has force-extension characteristics that are compatible with the force-extension characteristics of the surrounding tissue, so that the flexibility of the surrounding tissue is not substantially restricted. Such force-extension characteristics, i.e., the mesh force-extension characteristics after the substantial degradation of the absorbable component is referred to herein as the "long-term force-extension characteristics." Similarly, the terms "long-term burst strength," "long-term residual mass" and "long-term average pore size," as used herein, refer to the burst strength, the residue mass and the average pore size of the mesh after the substantial degradation of the absorbable component. Depending on the type of the absorbable fiber, the substantial degradation of the absorbable component may take 3-12 months. Therefore, in some embodiments, the "long-term force-extension characteristics" refer to force-extension characteristics of a polymeric mesh at 12 months after implantation.

The term "non-absorbable fiber" as used herein, refers to a fiber made from one or more non-absorbable polymers. The non-absorbable fiber may be a multifilament fiber, a monofilament fiber, or combinations thereof. A "non-absorbable polymer" is a polymer that is completely or substantially incapable of being absorbed, either fully or partially, by tissue after introduction into a live subject. A non-absorbable or non-biodegradable polymer serves a permanent function in the body, such as supporting damaged or weakened tissue.

Examples of non-absorbable polymers include, but are not limited to, polyethylene, polypropylene, polyester, polytetrafluoroethylene (PTFE) such as that sold under the registered trademark TEFLON™ by E.I. DuPont de Nemours & Co., expanded PTFE (ePTFE), polyurethane, polyamide, nylon, polyetheretherketone (PEEK), polysulfone, fiberglass, an acrylic, polyvinyl alcohol, or any other medically acceptable yet non-absorbable fiber. In certain embodiments, the non-absorbable polymers are synthetic polymers. In one embodiment, the non-absorbable fiber comprises polyethylene. In another embodiment, the non-absorbable fiber comprises polypropylene.

As used herein, the term "synthetic polymer" refers to polymers that are chemically synthesized in a laboratory or an industry setting. The term "synthetic polymer" does not include naturally produced polymers such as silk or silk fibroin.

The term "absorbable fiber" as used herein, refers to a fiber made from one or more "absorbable polymers." The absorbable fiber may be a multifilament fiber, a monofilament fiber, or combinations thereof. The term "absorbable polymer" refers to a polymer that can be broken down by either chemical or physical process, upon interaction with the physiological environment at the implantation site, and erodes or dissolves within a period of time. The rate of degradation is mostly determined by the chemical structure of the polymer, as well as the local environment after implantation. While some absorbable polymers, such as lactide/glycolide polymers, can be substantially degraded within weeks of implantation, other absorbable polymers, such as silk, are degraded slowly over a period of months or years after implantation. An absorbable polymer serves a temporary function in the body, such as closing a varicose vein, supporting or seal a lumen or delivering a drug, and is then degraded or broken into components that are metabolizable or excretable.

Examples of absorbable polymers include, but are not limited to, polyglycolic acid (PGA), polylactic acid (PLA), lactic acid-glycolic acid copolymer (PLGA), polyhydroxyalkanoates (PHA), polyhydroxybutyrate-valerate (PHBV), polyvinyl alcohol (PVA), polyethylene terephthalate (PET), polyglycolide-lactide, polycaprolactone (PCL), lactic acid-ε-caprolactone copolymer (PLCL), polydioxanone (PDO), polytrimethylene carbonate (PTMC), poly(amino acid), polydioxanone, polyoxalate, a polyanhydride, a poly(phosphoester), polyorthoester and copolymers thereof, catgut suture, collagen, silk, chitin, chitosan, poly hyaluronic acid, or any other medically acceptable yet absorbable fiber.

Other suitable absorbable polymers include, but are not limited to, segmented, aliphatic polyether-ester urethanes (APEEU) and polyether-ester-carbonate urethanes (APEECU), as well as absorbable polyester copolymers or mixtures thereof.

Suitable APEEUs and APEECUs comprise polyoxyalkylene chains (such as those derived from polyethylene glycol and block or random copolymers of ethylene oxide and propylene oxide) covalently linked to polyester or polyester-carbonate segments (derived from at least one monomer selected from the group represented by trimethylene carbonate, c-caprolactone, lactide, glycolide, p-dioxanone, 1,5-dioxepan-2-one, and a morpholinedione) and interlinked with aliphatic urethane segments derived from 1,6 hexamethylene-, 1-4 cyclohexane-, cyclohexane-bismethylene-, 1,8 octamethylene- or lysine-derived diisocyanate.

Suitable absorbable polyester copolymers include, but are not limited to, lactide/glycolide copolymers, caprolactone/glycolide copolymers, lactide/trimethylene carbonate copolymers, lactide/glycolide/caprolactone tripolymers, lactide/glycolide/trimethylene carbonate tripolymers, lactide/caprolactone/trimethylene carbonate tripolymers, glycolide/caprolactone/trimethylene carbonate tripolymers, and lactide/glycolide/caprolactone/trimethylene carbonate terpolymers.

In other embodiments, the absorbable polymer fiber comprises polyaxial, segmented co-polymers with non-crystallizable, flexible components of the chain at the core and rigid, crystallizable segments at the chain terminals. The absorbable polymers are produced by reacting amorphous polymeric polyaxial initiators with cyclic monomers. The amorphous polymeric polyaxial initiators have branches originating from a polyfunctional organic compound so as to extend along more than two coordinates and to copolymerize with the cyclic monomers. In some embodiments, the absorbable copolymer comprises at least 30%, 50%, 65%, 75%, 90% or 95% by weight, of a crystallizable component which is made primarily of glycolide-derived or l-lactide-derived sequences.

In some embodiments, the amorphous polymeric, polyaxial initiators are made by reacting a cyclic monomer or a mixture of cyclic monomers such as trimethylene carbonate (TMC), caprolactone, and 1,5-dioxapane-2-one in the presence of an organometallic catalyst with one or more polyhydroxy, polyamino, or hydroxyamino compound having three or more reactive amines and/or hydroxyl groups. Typical examples of the latter compounds are glycerol and ethane-trimethylol, propane-trimethylol, pentaerythritol, triethanolamine, and N-2-aminoethyl-1,3-propanediamine.

The flexible polyaxial initiator can be derived from p-dioxanone, 1,5-dioxepan-2-one, or one of the following mixtures of polymers: (1) trimethylene carbonate and 1,5-dioxepan-2-one with or without a small amount of glycolide; (2) trimethylene carbonate and a cyclic dimer of 1,5-dioxepan-2-one with or without a small amount of glycolide; (3) caprolactone and p-dioxanone with or without a small amount of glycolide; (4) trimethylene carbonate and caprolactone with or without a small amount of dl-lactide; (5) caprolactone and dl-lactide (or meso-lactide) with or without a small amount of glycolide; and (6) trimethylene carbonate and dl-lactide (or meso-lactide) with or without a small amount of glycolide. Further, the crystallizable segment can be derived from glycolide or l-lactide. Alternate precursors of the crystallizable segment can be a mixture of predominantly glycolide or l-lactide with a minor component of one or more of the following monomers: p-dioxanone, 1,5-dioxepan-2-one, trimethylene carbonate, and caprolactone.

In other embodiments, the absorbable polymer is an ABA-type tripolymer, where A is l-lactide/glycolide and B is PEG. In certain embodiments, the absorbable polymer fiber comprises a polyaxial, segmented biodegradable copolyester. In other embodiments, the absorbable polymer comprises a l-lactide/caprolactone copolymer, a l-lactide/trimethylene carbonate coploymer, a glycolide/l-lactide/trimethylene carbonate copolymer coploymer, a l-lactide/caprolactone/trimethylene carbonate coploymer or combinations thereof. In one embodiment, the absorbable polymer comprises a homopolymer of polydioxanone. In another embodiment, the absorbable polymer comprises a glycolide/l-lactide/trimethylene carbonate copolymer. In another embodiment, the absorbable polymer comprises a PEG/glycolide/l-lactide copolymer.

In some embodiments, the absorbable polymer is an uniaxial polymer. Examples of uniaxial polymers include, but are not limited to, a homopolymer of polydioxanone, poly glycolic acid, polyglycolide, polylactide (L-, D-, or meso-), trimethylene carbonate, polycaprolactone, and copolymers thereof.

The non-absorbable fiber or the absorbable fiber can be a monofilament fiber, a multifilament fiber, or combinations thereof. In one embodiment, the absorbable fiber has a denier range of 25-200 g/9000 m. In another embodiment, the non-absorbable fiber has a denier range of 60-150 g/9000 m. Monofilament-based meshes have marked stiffness, whereas multifilament meshes have improved softness, less surface texture, and better drape characteristics for adaptation to anatomical curvatures. Multifilaments physically have a pronounced increase in surface area, which influences their biocompatibility. In certain embodiments, both the non-absorbable fiber and the absorbable fiber are multifilament fibers. In some embodiments, both the non-absorbable fiber and the absorbable fiber are non-braided multi-filament fibers. In other embodiments, the absorbable fiber has an ultimate elongation that is equal to or less than an ultimate elongation of said non-absorbable fiber. The term "ultimate elongation" refers to the strain at break determined as a percentage with respect to the original length.

In some embodiments, the multifilament fiber comprises microfibers of different diameters. In one embodiment, the multifilament fiber comprises a first set of microfibers having diameter in the range of 15-25 microns (2-3 denier per filament, typical fiber count is 60-100 filaments to produce a single end of fiber)) and a second set of microfibers having diameter in the range of 30-50 microns (12-18 denier per filament, typical fiber count is 5-15 filaments to produce a single end of fiber).

In other embodiments, one of the non-absorbable fiber and the absorbable fiber is a monofilament fiber. In yet other embodiments, both of the non-absorbable fiber and the absorbable fiber are monofilament fibers.

In certain embodiments, the polymeric mesh does not contain natural polymers such as silk yarn or silk fibroin. As used herein, the term "silk" refers to the natural protein fiber produced by inserts, such as the larvae of the mulberry silkworm, certain bees, wasps, ants and various arachnids.

Mesh Structure

The polymeric mesh of the instant application is a warp knit mesh. The mechanical properties of a knitted structure are largely dependent on the interaction of each stitch with its neighboring stitches in the course and wale directions. The course is the cross direction to the fabric production, while the wale is the parallel direction to the fabric production.

The warp structure, on the other hand, is a sheet of fiber with ends wrapped concentrically in parallel on a cylindrical beam prepared in a creel prior to being mounted on the knitting machine. The warp fibers lap the needle bar simultaneously by a series of guide bars that move through and then laterally to the needle bar. Lateral movements include underlaps which are produced on the mesh production side of the needle bar and overlap on the alternate side. The number of guide bars is pattern-specific but generally varies between one and four. Warp knit meshes provide versatile pattern selection, control of elasticity, unraveling resistance, good drapability, control of porosity, good dimensional stability. In some embodiments, the polymeric mesh contains absorbable fiber warp knitted in a 2 bar marquisette pattern and non-absorbable fiber knitted in a 2 bar sand-fly net pattern with all guide bars for each pattern threaded 1-in and 1-out.

Mesh Properties

Mesh properties include mesh composition, force-extension characteristics, porosity, thickness and area weight, all which clinically translate into surgical handling characteristics, anatomical conformability, foreign body reaction, and the mechanical, cellular, and extra cellular matrix characteristics of the mesh/tissue complex.

Composition

In some embodiments, the polymeric mesh of the present application contains an absorbable component and a non-absorbable component. In some embodiments, the mesh is co-knitted with an absorbable fiber and a non-absorbable fiber. The fibers are co-knitted at an absorbable fiber-to-non-absorbable fiber weight ratio in the range of 1:5 to 5:1, 1:4 to 4:1, 1:3 to 3:1 or 1:2 to 2:1. In one embodiment, the fibers are co-knitted at an absorbable fiber-to-non-absorbable fiber weight ratio of 1:1. In some embodiments, the absorbable fiber is a monofilament fiber, a multifilament fiber, or a combination thereof, and has a denier range of 25-250 g/9000 m, 25-200 g/9000 m, 50-250 g/9000 m, or 100-170 g/9000 m. The non-absorbable fiber is a monofilament fiber, a multifilament fiber, or a combination thereof, and has a denier range of 30-200 g/9000 m or 60-150 g/9000 m. In some embodiments, the absorbable fiber constitutes about 30-60% by weight of the polymeric mesh, which results in a long-term the residual mass will be approximately 40-70% of the initial mass.

Force-Extension Characteristics

The polymeric mesh of the instant application provides an initial high level of structural stiffness. Upon substantial degradation of the absorbable fiber, the mesh comprised of the non-degrading fiber is liberated and affords high compliance. Preferably, the mesh comprised of only the non-degrading fiber has force-extension characteristics that are compatible with the elasticity of the surrounding tissue, so that the flexibility of the surrounding tissue is not substantially restricted. The force-extension characteristics of a polymeric mesh include, but are not limited to, tensile properties such as tensile extension, and burst properties such as burst pressure/strength, burst force, and burst extension.

In some embodiments, the absorbable fiber is substantially degraded within a time period of 1-2 weeks, 2-4 weeks, 1-2 months, 2-4 months or 4-9 months. The time of substantial degradation herein is defined as the point in time at which the material substantially loses its mechanical properties, or its mechanical integrity, even though fragments of the material may still be present in the body. In the present application, the substantial degradation of the absorbable fiber initiates the load transition period (LTP) for the mesh to modulate from a mode of stress shielding the encapsulating extra-cellular matrix (ECM) and surrounding tissue to transmitting, in part, applied stresses. In some embodiments, the absorbable fiber is substantially degraded when over 50%, 60%, 70%, 80% or 90% of the absorbable fiber is degraded. In other embodiments, the absorbable fiber is substantially degraded when the absorbable fiber losses over 50%, 60%, 70%, 80% or 90% of its initial strength, as measured by the burst force of the polymeric mesh at the time of implantation and the time of substantial degradation.

Tensile Extension

Tensile extension reflects the uniaxial extension characteristics of a mesh material and can be used to evaluate the resistance to deformation of the polymeric mesh of the instant application at the early phase of the implantation, i.e., when the absorbable component of the mesh has not been substantially degraded. In some embodiments, the polymeric mesh of the present application has an initial tensile extension at 16 N/cm (i.e., the tensile extension before implantation) in the range of 0-40%, 0-35%, 0-30% or 0-25% in both the wale (machine) and course (cross-machine) directions. Tensile extension is determined with the method described in Example 6.

Burst Pressure, Burst Force, Burst Strength and Burst Extension

The burst properties reflect the multiaxial extension characteristics of a mesh material. The burst pressure is the maximum pressure which the polymeric mesh can endure before it breaks. In certain embodiments, the polymeric mesh of the instant application has burst pressure in the range of 150 kPa to 4 MPa, measured according to ASTM D3786. In other embodiments, the polymeric mesh of the instant application has burst pressure in the range of 300 kPa to 2 MPa, measured according to ASTM D3786. In other embodiments, the polymeric mesh of the instant application has burst pressure in the range of 450 kPa to 1.5 MPa, measured according to ASTM D3786. In yet other embodiments, the polymeric mesh of the present application has burst pressure in the range of 590 kPa to 1.2 MPa, measured according to ASTM D3786.

The burst force describes the load at which the mesh will burst using the method as indicated in ASTM D 3787-07 standard test method for bursting strength of textiles-constant-rate-of-traverse ball burst test. In some embodiments, the polymeric meshes of the present application have a minimum initial burst force of 200 N, 250 N, 300 N, 350 N or 400 N, and a long-term burst force of at least 140 N, 160 N, 180 N or 200 N.

The burst extension is the percentage of extension of a test material under a given burst force load and is measured as described in Example 6. In some embodiments, the polymeric mesh of the present application has an initial burst extension at 16 N/cm (i.e., the burst extension before implantation) in the range of 0-11%, 0-10%, 0-9% or 0-8%.

The polymeric mesh of the instant application has long-term force-extension characteristics compatible with surrounding tissues at an implantation site. As used herein, "long-term force-extension characteristics" of a polymeric mesh refer to the force-extension characteristics of the polymeric mesh 12 months after implantation. In some embodiments, the polymeric mesh is considered to have long-term force-extensional characteristics compatible with surrounding tissues, if the long-term force-extensional characteristics of the polymeric mesh is within the range of 50%-150% of the corresponding force-extensional characteristics of the surrounding tissue at the implantation site. If the implantation site contains multiple tissue types, the "surrounding tissue" is the tissue that has the largest weight percentage among all the tissues at the implantation site.

For example, if the polymeric mesh of the present application is implanted at the abdominal wall which has a burst extension range of 18%-32% at 16 N/cm, measured as described in Example 6, the polymeric mesh would be considered to have long-term force-extensional characteristics compatible with surrounding tissues if the polymeric mesh has a long-term burst extension within the range of 9%-48%.

In other embodiments, the polymeric mesh is considered to have long-term force-extension characteristics compatible with surrounding tissues, if the long-term burst extension range of the polymeric mesh is within 25%-200%, 40%-180%, 75%-125% or 90%-110% of the force-extension range of the surrounding tissue at the implantation site.

Porosity

Porosity is a key factor in the incorporation of the mesh into the surrounding tissue, and thus an important prerequisite to its biocompatibility. The total porosity of the polymeric mesh of the instant application may be described as the amount of open space in a unit area of mesh (expressed as the percentage of open space in a given area). The overall porosity, such as dimensions/area of individual pores, the distance between pores, and the size and quantity of interstitial pores, may be determined using digital imaging. In some embodiments, the polymeric mesh of the instant application has a total porosity in the range of 10%-60% with an average initial pore size of about 0.2-5 mm. In other embodiments, the polymeric mesh of the instant application has a total porosity in the range of 20%-50% with an average initial pore size of about 0.5-2 mm. In other embodiments, the polymeric mesh of the instant application has a total porosity in the range of 30%-40% with an average initial pore size of about 1 mm. In another embodiment, the polymeric mesh has a total porosity within the range of 30-40% with an initial average pore size of about 1 mm and a long-term average pore size of about 2-3 mm.

In some embodiments, the initial polymeric mesh allows an elongation of no more than 10%, 20% or 30%, and the residual polymeric mesh (i.e., after the degradation of the absorbable fiber) allows an elongation of 40-90%. Preferably, the residual polymeric mesh is designed to have an elongation range that is compatible with the elasticity of the surrounding tissue. In one embodiment, the absorbable fiber has an ultimate elongation in the range of 40-90%, preferably 50-80%, while the non-absorbable fiber has an ultimate elongation of greater than 30%, preferably 40-80%.

In some other embodiments, the absorbable fiber has a modulus of elasticity that is significantly higher than the modulus of elasticity of the non-absorbable fiber.

Thickness

In some embodiments, the polymeric meshes of the instant application have a thickness in the range of 0.1 mm-2 mm. In other embodiments, the polymeric meshes of the instant application have a thickness in the range of 0.2 mm-1 mm. In other embodiments, the polymeric meshes of the instant application have a thickness in the range of 0.3 mm-0.5 mm. In yet other embodiments, the polymeric meshes of the instant application have a thickness of about 0.4 mm.

Area Weight

Area weight, measured as the mass per area (g/m2), is a determination of the total amount of biomaterial implanted for a given area. Theoretically, lower area weights induce a milder foreign body reaction, improved tissue compliance, less contraction or shrinkage, and allow better tissue incorporation. In some embodiments, the polymeric meshes of the instant application have an initial area weight with values ranging from 20 to 160 g/m$^2$. In other embodiments, the polymeric meshes of the instant application have an initial area weight with values ranging from 50 to 130 g/m$^2$. In other embodiments, the polymeric meshes of the instant application have an initial area weight with values ranging from 70 to 110 g/m$^2$. In yet other embodiments, the polymeric meshes of the instant application have an initial area weight with values ranging from 70 to 80 g/m$^2$.

Mesh Properties as Determined from Materials

The force-extension, strength, load transition period (LTP), and absorption/degradation rate of the absorbable component of the polymeric mesh of the present application is controlled by the polymeric materials that constitute the absorbable fiber and non-absorbable fiber. The force-extension properties are, in part, controlled by mesh materials, but to a significantly lower degree than the influence of mesh construction. Material properties are a major player in mesh strength. The chemistry of the absorbable component dictates the LTP which is critical to efficacy. Some polymeric materials are more elastic and/or stronger than other polymeric materials. Accordingly, polymeric meshes with desired extensibility, strength and degradation profile may be constructed using the proper polymeric materials or combinations thereof.

For example, polyglycolide is a fast-degrading polymer with substantial loss in mechanical properties within 1 month and complete mass loss within 6-12 months, while poly(1-lactide) has a much slower degradation rate, typically requiring greater than 24 months to achieve substantial degradation. Silk has an even slower degradation rate and requires several years or even longer to achieve substantial degradation. The desired degradation period may be achieved by using the proper polymers, co-polymers or mixtures thereof.

Mesh Properties as Determined from Knitting

The force-extension characteristics of the polymeric mesh of the present application is also controlled by the knitting parameters. For example, the force-extension characteristics of a mesh is controlled by the number of needles per inch, i.e. gauge, and the stitch length, which controls the number of courses per inch. The gauge is typically set by the chosen machine configuration leaving the stitch length as the only adjustable variable. Although force-extension characteristics can be somewhat adjusted using these parameters, knit pattern structural variability is the primary variable that can be used to modify warp knit properties.

The variability available with warp knitting allows extensive modulation of the physical and mechanical properties. Traditionally, to produce elastic or stretchable structures, the mesh must be designed with either (1) short underlaps or (2) an open mesh construction. The most basic example of short underlaps is a single guide bar, one needle underlap and one needle overlap, commonly referred to as a half-tricot stitch. Increases in the underlap movement reduce extensibility and increase stability. The half tricot pattern produces a dimensionally stretchable mesh with relatively small pores. To produce larger openings in the mesh, loops can be formed continuously on the same needle such that there are no connections by adjacent wales (underlaps) followed by a lateral interlace after a specific number of courses. Different size and shape openings can be produced with symmetrical pores when knit using partial threading of two guide bars that are lapping in opposition. Another significantly less extensible open work mesh that can be created is a simple chain stitch which is interconnected using a lay-in fiber to connect adjacent wales, i.e. a marquisette construction. The polymeric mesh mechanical properties of the present application are controlled by the interdependent, co-knit construction of the respective knit patterns of the absorbable fiber and non-absorbable fiber which affords an additional method of modulating physical and mechanical properties.

Bioactive Agents

The polymeric mesh of the present application may further comprises one or more bioactive agents. The bioactive agents may be applied to one or more specific section of the mesh, as opposed to the entire mesh. Within certain embodiments, the mesh can be either dip-coated or spray-coated with one or more bioactive agents, or with a composition which releases one or more bioactive agents over a desired time frame. Within yet other embodiments, the fibers themselves may be constructed to release the bioactive agent(s) (see e.g., U.S. Pat. No. 8,128,954 which is incorporated by reference in its entirety).

Examples of such bioactive agents includes, but are not limited to, fibrosis-inducing agents, antifungal agents, antibacterial agents and antibiotics, anti-inflammatory agents, anti-scarring agents, immunosuppressive agents, immunostimulatory agents, antiseptics, anesthetics, antioxidants, cell/tissue growth promoting factors, anti-neoplastic, anticancer agents and agents that support ECM integration.

Examples of fibrosis-inducing agents include, but are not limited to talcum powder, metallic beryllium and oxides thereof, copper, silk, silica, crystalline silicates, talc, quartz dust, and ethanol; a component of extracellular matrix selected from fibronectin, collagen, fibrin, or fibrinogen; a polymer selected from the group consisting of polylysine, poly(ethylene-co-vinylacetate), chitosan, N-carboxybutyl-chitosan, and RGD proteins; vinyl chloride or a polymer of vinyl chloride; an adhesive selected from the group consisting of cyanoacrylates and crosslinked poly(ethylene glycol)-methylated collagen; an inflammatory cytokine (e.g., TGFβ, PDGF, VEGF, bFGF, TNFα, NGF, GM-CSF, IGF-a, IL-1, IL-1-β, IL-8, IL-6, and growth hormone); connective tissue growth factor (CTGF); a bone morphogenic protein (BMP) (e.g., BMP-2, BMP-3, BMP-4, BMP-5, BMP-6, or BMP-7); leptin, and bleomycin or an analogue or derivative thereof. Optionally, the device may additionally comprise a proliferative agent that stimulates cellular proliferation. Examples of proliferative agents include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. (see US 2006/0240063, which is incorporated by reference in its entirety).

Examples of antifungal agents include, but are not limited to, polyene antifungals, azole antifungal drugs, and Echinocandins.

Examples of antibacterial agents and antibiotics include, but are not limited to, erythromycin, penicillins, cephalosporins, doxycycline, gentamicin, vancomycin, tobramycin, clindamycin, and mitomycin.

Examples of anti-inflammatory agents include, but are not limited to, non-steriodal anti-inflammatory drugs such as ketorolac, naproxen, diclofenac sodium and fluribiprofen.

Examples of anti-scarring agents include, but are not limited to cell-cycle inhibitors such as a taxane, immunomodulatory agents such as serolimus or biolimus (see, e.g., paras. 64 to 363, as well as all of US 2005/0149158, which is incorporated by reference in its entirety).

Examples of immunosuppressive agents include, but are not limited to, glucocorticoids, alkylating agents, antimetabolites, and drugs acting on immunophilins such as ciclosporin and tacrolimus.

Examples of immunostimulatory agents include, but are not limited to, interleukins, interferon, cytokines, toll-like receptor (TLR) agonists, cytokine receptor agonist, CD40 agonist, Fc receptor agonist, CpG-containing immunostimulatory nucleic acid, complement receptor agonist, or an adjuvant.

Examples of antiseptics include, but are not limited to, chlorhexidine and tibezonium iodide.

Examples of anesthetic include, but are not limited to, lidocaine, mepivacaine, pyrrocaine, bupivacaine, prilocalne, and etidocaine.

Examples of antioxidants include, but are not limited to, antioxidant vitamins, carotenoids, and flavonoids.

Examples of cell growth promoting factors include, but are not limited to, epidermal growth factors, human platelet derived TGF-β, endothelial cell growth factors, thymocyte-activating factors, platelet derived growth factors, fibroblast growth factor, fibronectin or laminin.

Examples of antineoplastic/anti-cancer agents include, but are not limited to, paclitaxel, carboplatin, miconazole, leflunamide, and ciprofloxacin.

Examples of agents that support ECM integration include, but are not limited to, gentamicin.

It is recognized that in certain forms of therapy, combinations of agents/drugs in the same mesh can be useful in order to obtain an optimal effect. Thus, for example, an antibacterial and an anti-inflammatory agent may be combined in a single copolymer to provide combined effectiveness. In some embodiments, one or more drugs (e.g., a fibrosis-inducing drug) are applied to only a specific section or area of the mesh, as opposed to the entire mesh. In other embodiments, two or more drugs are applied to two or more areas of the mesh.

Method of Making

The fibers of the meshes of the instant application can be made with any process commonly used in the art. In one embodiment, multifilament fiber is melt extruded using an extruder, metering pump, and die (specific to the fiber denier and number of filaments). The extruded fiber is in-line drawn with draw ratios from 1.5 to 3.3. Subsequent to the initial orientation developed during the extrusion, the fiber is typically drawn again in a more traditional "cold" draw using a draw ratio range of 1.1 to 1.5. This results in typical overall draw ratios from 1.7 to 5.0 (material dependent).

The fibers are then co-knitted into an interdependent mesh. In certain embodiments, one absorbable fiber and one non-absorbable fiber, or one fast-absorbable fiber and one slow-absorbable fiber, are co-knitted into an interdependent mesh. In some embodiments, the knit constructions are produced using a two step process of warping fiber onto beams and constructing meshes using a Raschel knitting machine or a Tricot knitting machine. In one embodiment, the knitting process utilizes two warped beams of fiber A threaded on bars 1 and 2 and two warped beams of fiber B threaded on bars 3 and 4. Fiber B is knit in a 2 bar marquisette pattern and fiber A knit in a 2 bar sand-fly net pattern with all guide bars for each pattern threaded 1-in and 1-out.

In some embodiments, the knitted mesh is subjected to a heat setting process that stabilizes mesh dimensional structure and refines the fiber microstructure morphology. The effect of heat setting is affected by the temperature, time, and tension applied during the process with the most significant factor being temperature. Fiber morphology is altered by relieving induced stress from orientation and increasing the fibers entropy. As a result, stresses in the construction of the mesh are relaxed which, in turn, lead to improved dimensional stability, heat stability from entropy driven shrinkage, handling characteristics, and in many cases the softness of the mesh.

In certain embodiments, heat setting was performed at 80-140° C. for 0.2-3 hours under vacuum (<10 torr) or at atmospheric pressure. In other embodiments, the heat setting was performed at 80-130° C. for 0.5-1.5 hour while under high vacuum (<1 torr) or at atmospheric pressure. In other embodiments, the heat setting was performed at 110-130° C. for 0.5-1.5 hour while under high vacuum (<1 torr) or at atmospheric pressure. In one embodiment, the heat setting was performed at about 110° C. for about 1 hour while under high vacuum (<1 torr) or at atmospheric pressure.

Method of Using

Another aspect of the present application relates to a method of treating a medical condition, such as hernia, urinary incontinence, prolapse and surgical or traumatic wounds, with the polymeric mesh of the present application. The method comprises the step of implanting into a patient a piece of the mesh of the present application at a treatment site. The implantation may be performed using conventional open or laproscopic procedures. Examples of open surgery procedures include, but are not limited to, the Lichtenstein procedure. Examples of laproscopic procedures include, but are not limited to, the trans-abdominal preperitoneal (TAPP) procedure and the total extraperitoneal (TEP) procedure. After implantation, the mesh implant can be fixed with for instance suitable sutures, staples, fixation, pins, adhesives or the like. In some applications of the implant, the pressure from the surrounding tissue may be enough for initial fixation until newly regenerating tissue anchors the implant by tissue through growth. In one embodiment, the method further comprises the step of securing the mesh at the treatment site.

The present invention is further illustrated by the following examples which should not be construed as limiting. The contents of all references, patents and published patent applications cited throughout this application, as well as the Figures and Tables are incorporated herein by reference.

EXAMPLES

FIG. 1 shows one of the objectives of the polymeric mesh of the present application, i.e., having modulate biomechanical properties that meet the expected needs of the wound healing process. To this end, several partially absorbable meshes have been developed which provides (1) short-term structural stiffness, (2) a gradual transition phase, and (3) long-term force-extensional properties similar to the tissue around the implantation site. As shown in FIG. 1, the short-term stiffness facilitates tissue stability during the development of wound strength; the gradual transfer of the mechanical loads from the mesh to the wounded tissue allows the wound to build mechanical integrity; and the compliance with the force-extensional properties of the surrounding tissue facilitates load transfer to the remodeling and maturing mesh/tissue complex; and minimizes the likelihood of long-term complications.

Example 1: Preparation of a Typical, Selectively Absorbable, Warp-Knitted Mesh Using Multifilament Fibers of Polyethylene (PE)

Fiber Preparation and Characteristics
 Fiber A (1-ply natural fiber of PE)
 Fiber Count: 80 to 100
 Denier Range: 60-150 g/9000 m
 Tenacity Range: >3 g/denier
 Ultimate Elongation: >30%
 Fiber B (1-ply natural fiber of an absorbable copolyester)
 Fiber Count: 5 or 10
 Denier Range: 100-170 g/9000 m
 Tenacity Range: >3 g/denier
 Ultimate Elongation: 50-80%
General Method for Composite Mesh Construction
 Selectively absorbable mesh (SAM) is comprised of two fibers (A and B), of which fiber A is non-absorbable and fiber B is absorbable. Each pattern is knit using a composite construction made from two individual patterns that coexist in one mesh. Knit constructions are produced using a two step process of warping fiber onto beams and constructing meshes using a Raschel knitting machine in the art. Knit constructions can be made from multifilament fiber, monofilament fiber, or combinations therefrom.

Subsequent to mesh knitting, knit mesh is heat set by stretching a tubular mesh over a stainless steel circular mandrel. To accommodate heat setting of the SAM mesh on circular mandrels, the flat mesh sheet is edge sewn into a tube using a standard sewing machine and high-strength polyethylene terephthalate fiber. Heat setting was completed at 110° C. for 1 hour while under high vacuum (<1 torr). Meshes were then cut from the mandrel to produce a stabilized sheet of mesh.

Knitting Process (Mesh Patterns)

The knitting process utilizes two warped beams of fiber A threaded on bars 1 and 2 and two warped beams of fiber B threaded on bars 3 and 4. The knitting machine is a Raschel knitting machine of 18 gauge needles. Fiber B is knit in a 2 bar marquisette pattern and fiber A knit in a 2 bar sand-fly net pattern with all guide bars for each pattern threaded 1-in and 1-out.

Knitting Pattern (28 courses per inch)
Bar 1—1-0/1-2/2-3/2-1//2x (1-in, 1-out)
Bar 2—2-3/2-1/1-0/1-2//2x (1-in, 1-out)
Bar 3—1-0/0-1//4x (1-in, 1-out)
Bar 4—0-0/3-3//4x (1-in, 1-out)

Typical Mechanical Properties

The resultant mechanical properties are based on the selection of Fiber B, as the degradation of this component determines the time at which the mesh transitions from a structurally stable/stiff construction to a more extensible/compliant construction. Minimum initial burst strength values of 300 N and a long-term burst strength of at least 180 N are typical and comparable to current clinically-relevant meshes.

Example 2: Preparation and Characterization of SAM3 Product

A selectively absorbable mesh (SAM3) with a load transition point of 3 weeks was prepared using the steps described in Example 1 with the following materials. Fiber B was constructed from a segmented poly-axial copolyester (92:8 95/5 Glycolide/L-lactide: poly-axial trimethylene carbonate, initiated with trimethylolpropane). Fiber A remains the same as in Example 1. The SAM3 product contains >50% of absorbable copolymer material, leaving a small amount of non-absorbable material for permanent implantation.

Figure 2A:
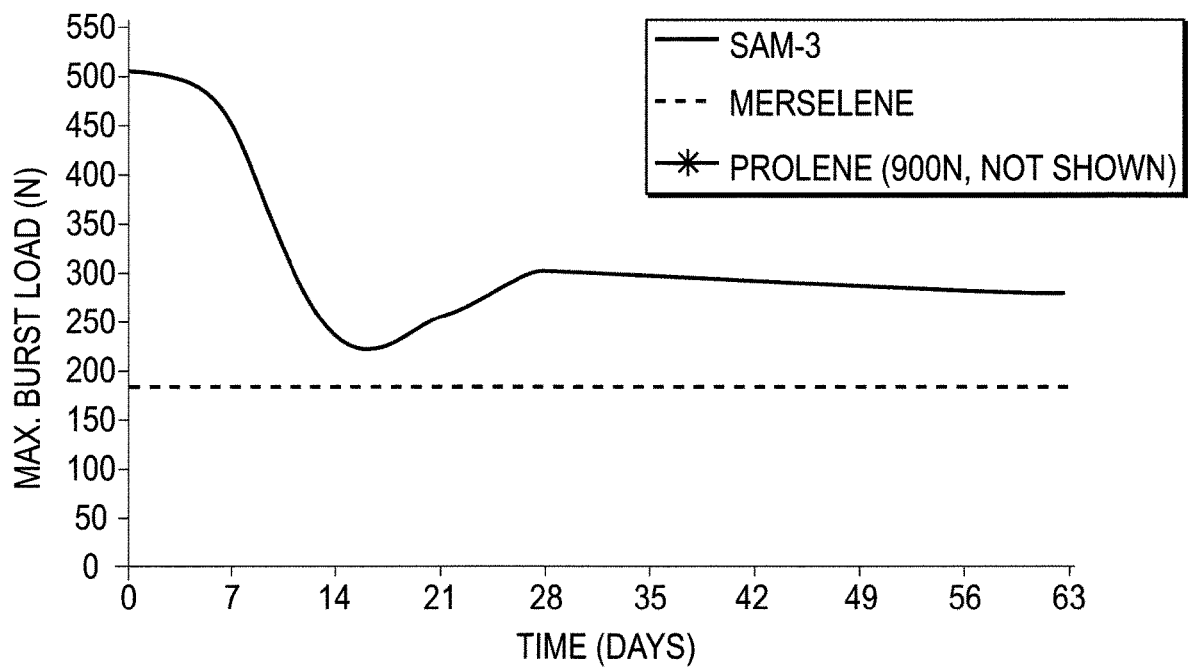
FIG. 2A is a diagram showing the strength retention of a polymeric mesh product of the present application after implantation.
Figure 2B:
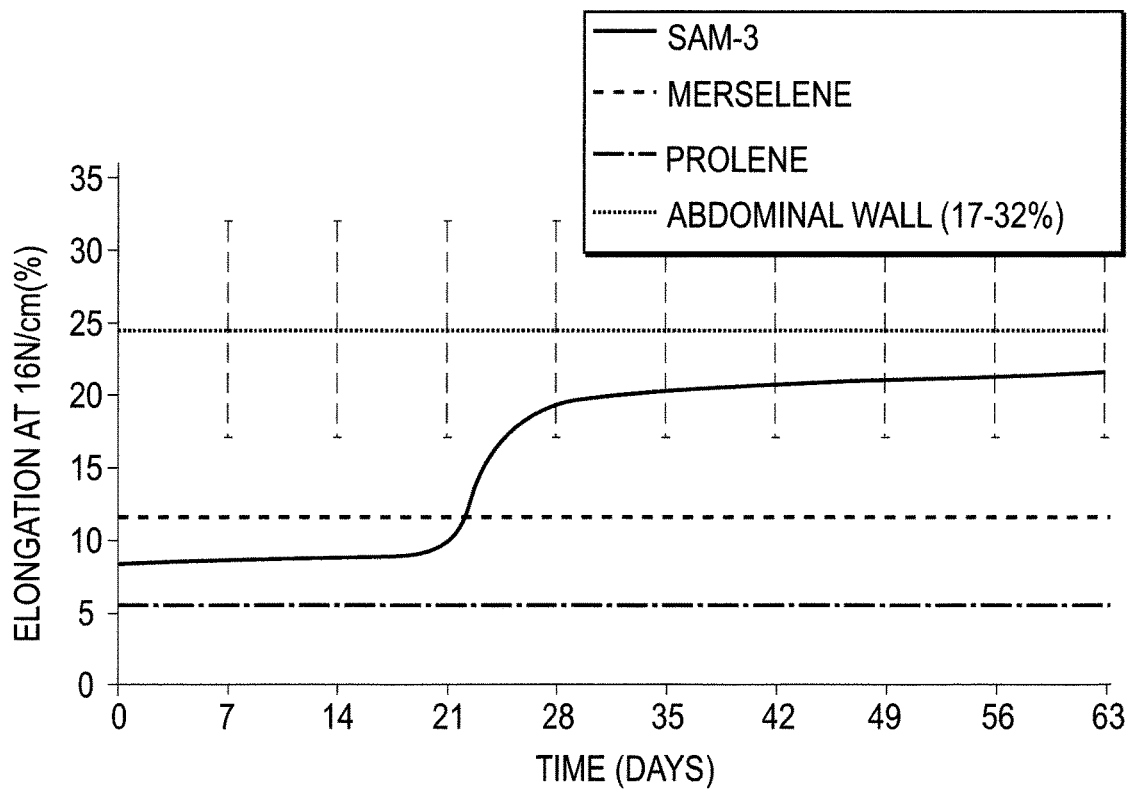
FIG. 2B is a diagram showing the elongation of the same polymeric mesh product after implantation.
Figure 2C:
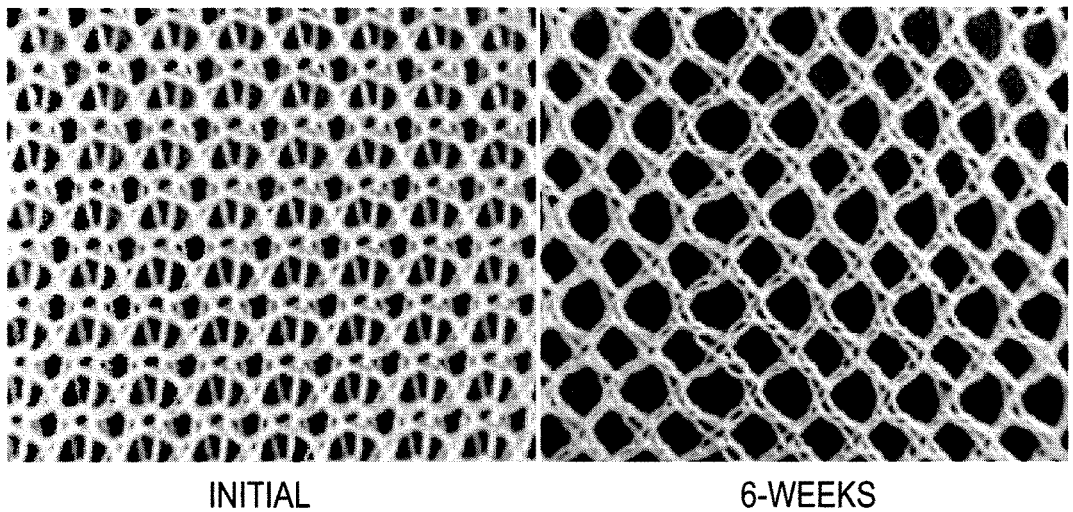
FIG. 2C shows the appearance of the same mesh product prior to implantation and 6 weeks after being exposed to conditions that simulate an in vivo environment.
Figure 2D:
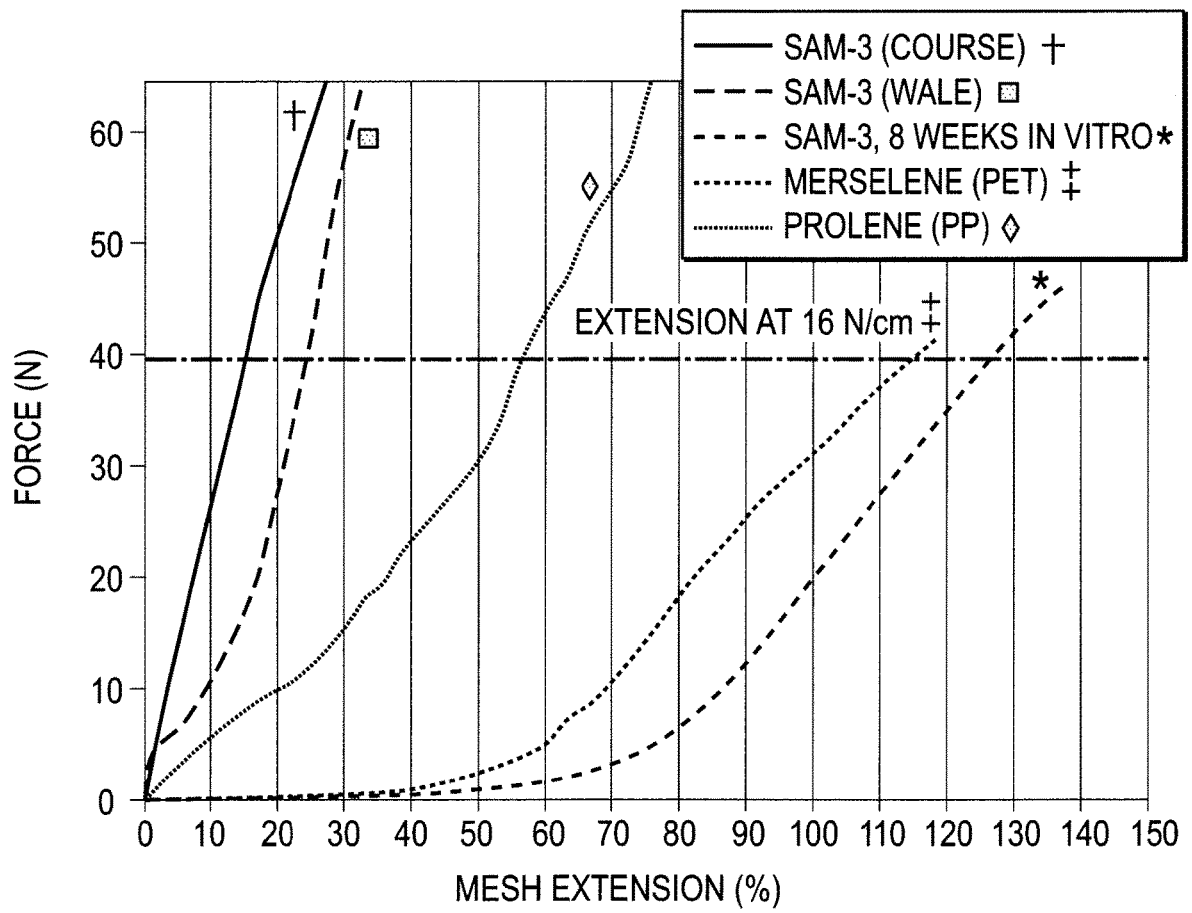
FIG. 2D shows the tensile properties (uniaxial) of the control products PP and PET meshes at 16 N/cm, and the tensile properties (uniaxial) of the SAM3 product at 16 N/cm before implantation and at various times after being exposed to conditions that simulate the in vivo environment.
Figure 2E:
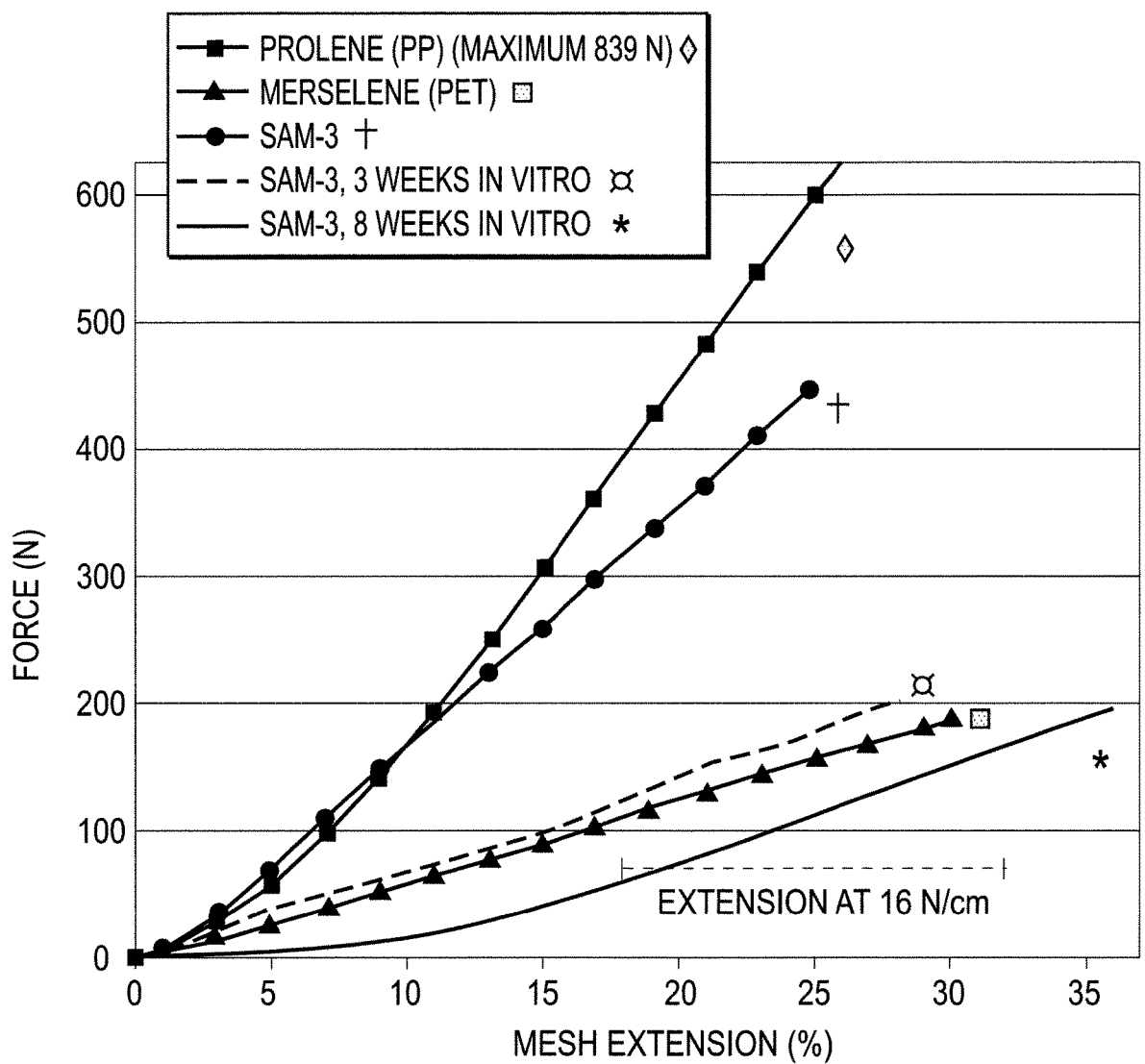
FIG. 2E shows the burst properties (multiaxial) of the control products PP and PET meshes at 16 N/cm, and the burst properties (multiaxial) of the SAM3 product at 16 N/cm before implantation and at various times after being exposed to conditions that simulate the in vivo environment.

As shown in FIGS. 2A and 2B, the SAM3 product has an initial burst stiffness and area weight comparable to current polypropylene (PP) meshes. The initial strength of the SAM3 product is almost 3 times the strength of MERSELENE® (PET) mesh (Ethicon). The elongation, however, almost doubles 4 weeks after implantation due to the degradation of the absorbable copolymer material in vivo. FIG. 2C shows the appearance of the mesh product prior to implantation and 6 weeks after being exposed to conditions that simulate the in vivo environment. FIG. 2D shows the tensile properties (uniaxial) of the control products PP and PET meshes at 16 N/cm, and the tensile properties (uniaxial) of the SAM3 product at 16 N/cm before implantation and at various times after being exposed to conditions that simulate the in vivo environment. FIG. 2E shows the burst properties (multiaxial) of the control products PP and PET meshes at 16 N/cm, and the burst properties (multiaxial) of the SAM3 product at 16 N/cm before implantation and at various times after being exposed to conditions that simulate the in vivo environment. As shown in FIG. 2E, SAM3 mesh's initial properties are similar to PP mesh in that both meshes show initial stability, representative by only ~5% mesh extension at the physiological abdominal wall force of 71 N. While PP mesh remains grossly outside of the physiological mechanical properties of the native abdominal wall, SAM3 mesh slowly transitions to match the biomechanics of the abdominal wall after the degradation of the absorbable component.

Example 3: Preparation of SAM4 Product

A selectively absorbable mesh (SAM4) with a load transition point of 5 weeks was prepared using the steps described in Example 1 with the following materials. Fiber B was constructed from a homopolymer of polydioxanone. Fiber A remains the same as in Example 1.

Figure 3A:
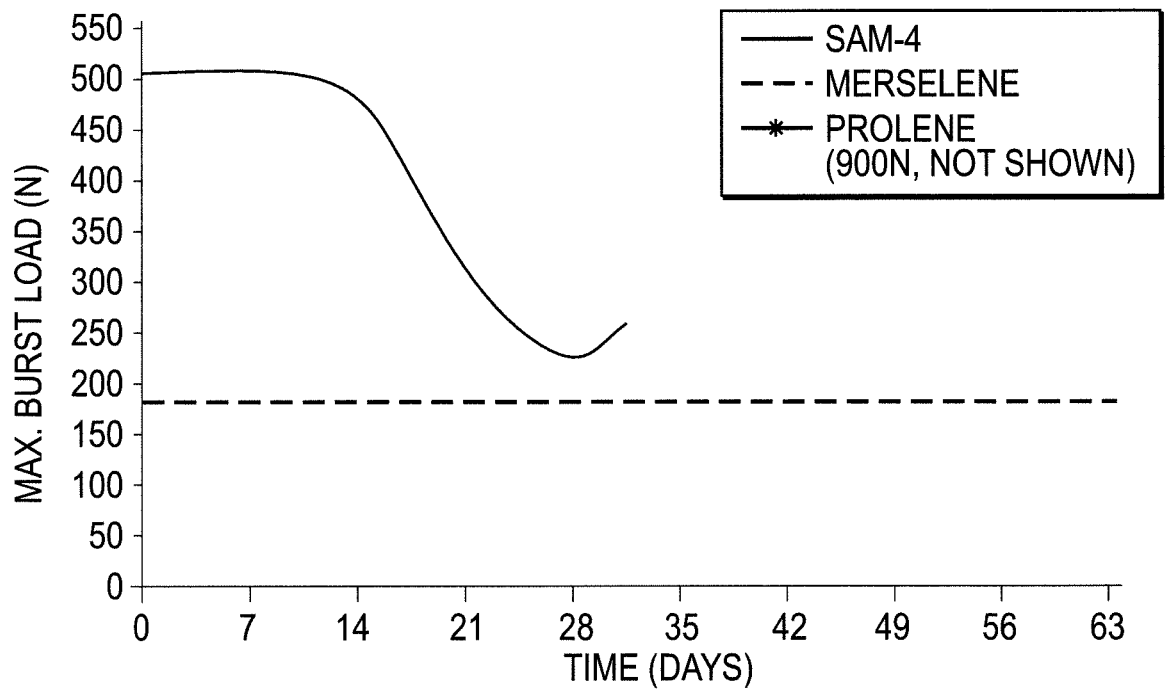
FIG. 3A is a diagram showing the strength retention of another polymeric mesh product of the present application after implantation.
Figure 3B:
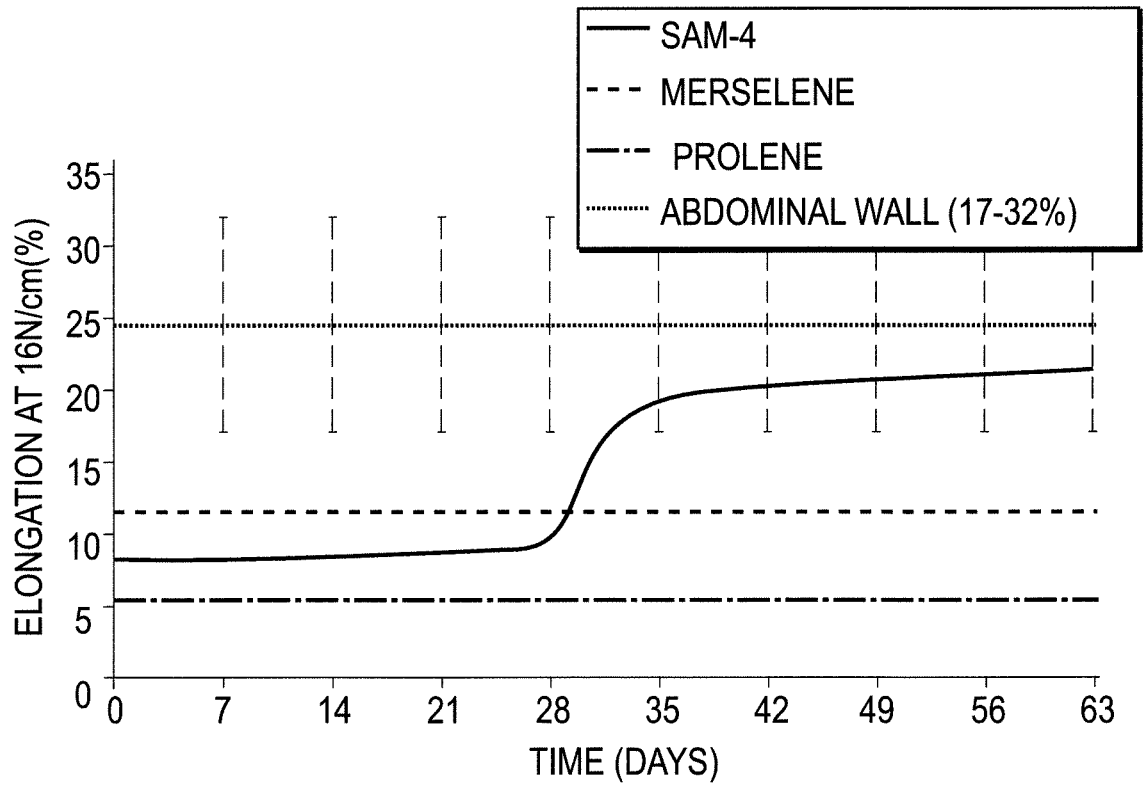
FIG. 3B is a diagram showing the elongation of the same polymeric mesh product after implantation.
Figure 3C:
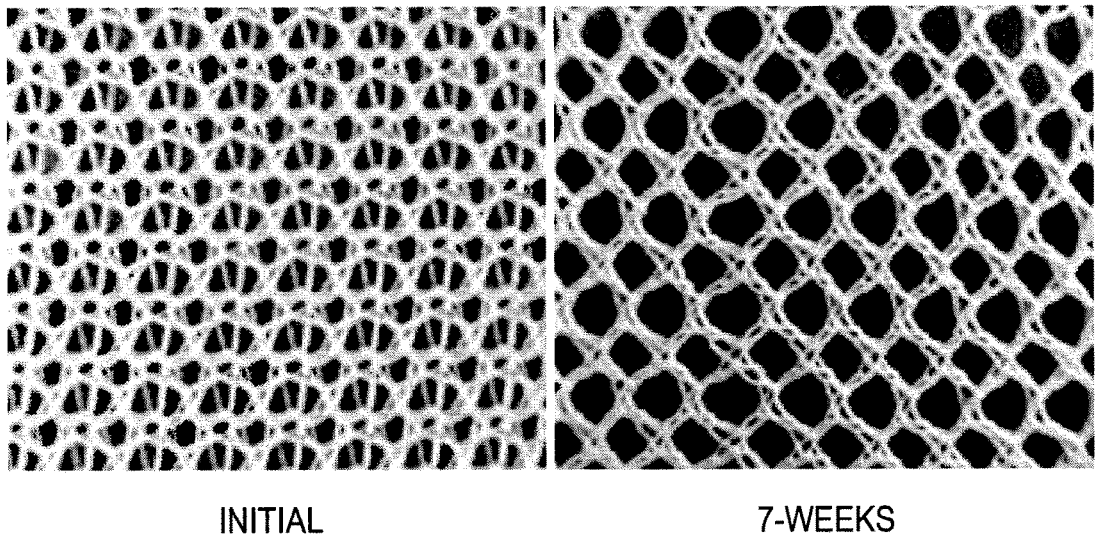
FIG. 3C shows the appearance of the same mesh product prior to implantation and 7 weeks after being exposed to conditions that simulate an in vivo environment.

As shown in FIGS. 3A and 3B, the SAM4 product has an initial stiffness and area weight comparable to current polypropylene (PP) meshes. The initial strength of the SAM4 product is almost 3 times the strength of Merselene® mesh (Ethicon). The elongation, however, almost doubles 5 weeks after implantation due to the degradation of the absorbable copolymer material in vivo. FIG. 3C shows the appearance of the mesh product prior to implantation and 7 weeks after being exposed to conditions that simulate the in vivo environment.

Example 4: Preparation of SAM8 Product

A selectively absorbable mesh (SAM8) with a load transition point of 8 weeks was prepared using the steps described in Example 1 with the following materials. Fiber B was constructed from a polymer consisting of an 8:92 of PEG 20,000: 94/6 L-lactide/glycolide. Fiber A remains the same as in Example 1.

Figure 4A:
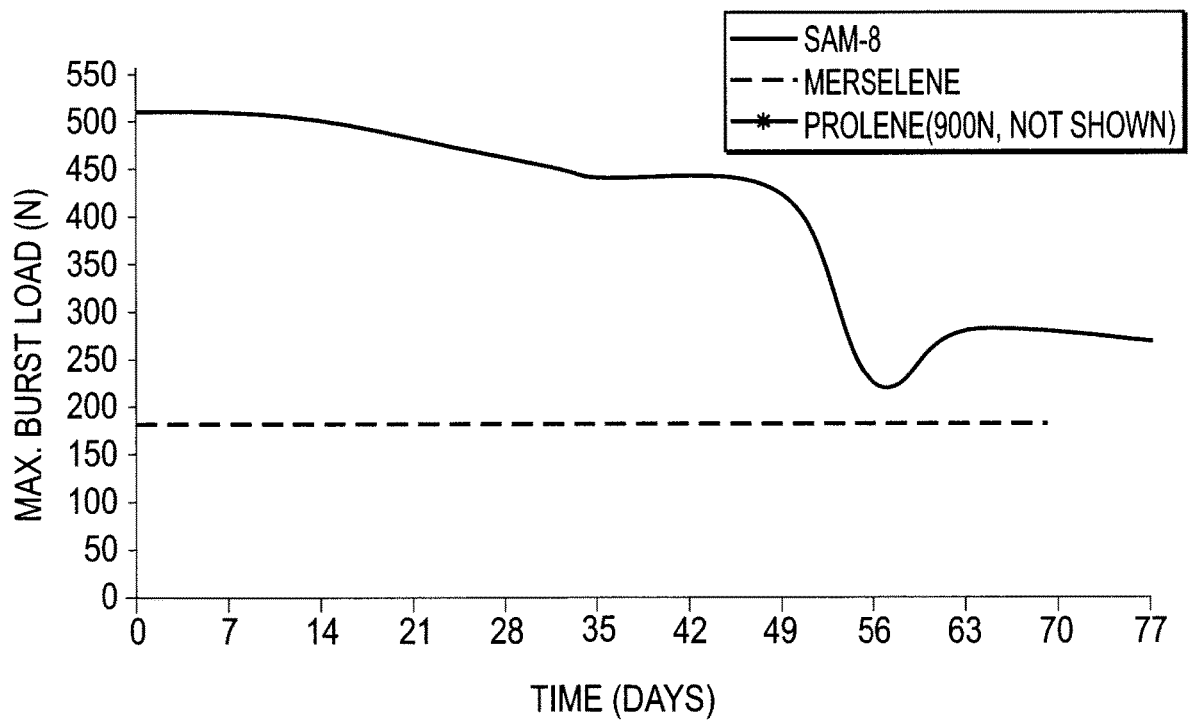
FIG. 4A is a diagram showing the strength retention of another polymeric mesh product of the present application after implantation.
Figure 4B:
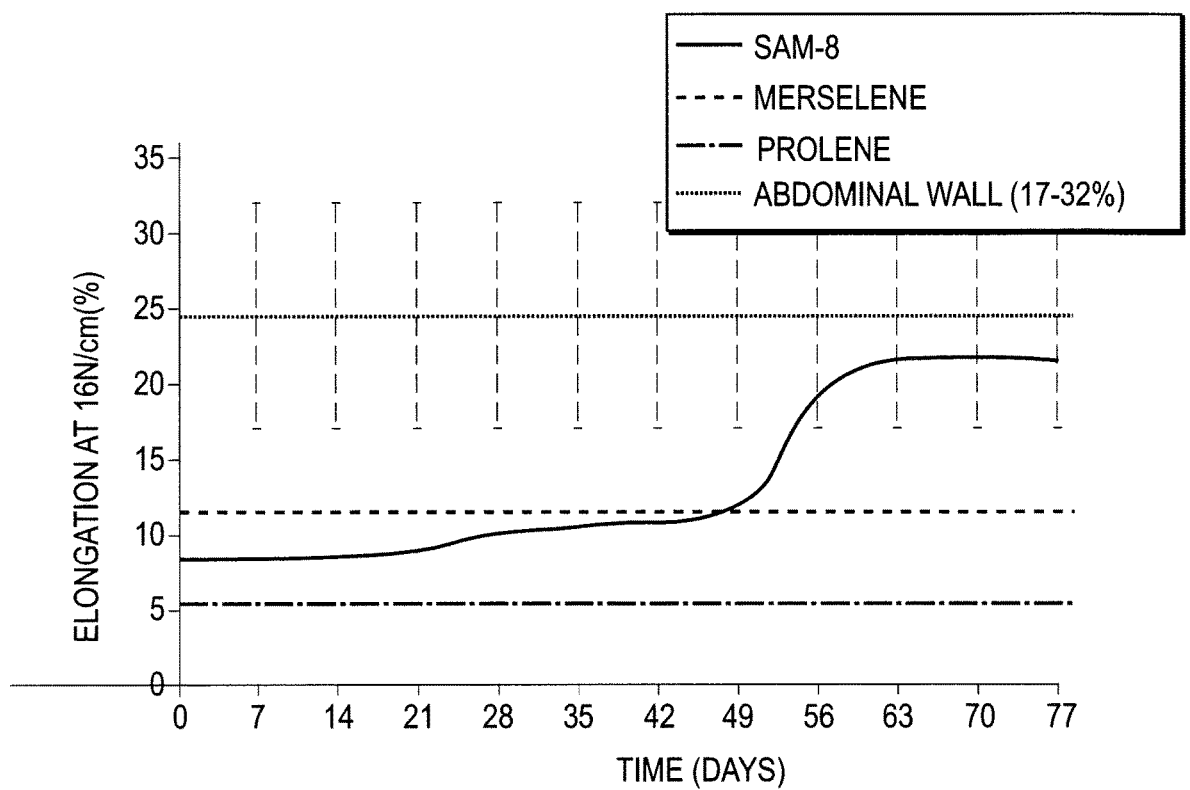
FIG. 4B is a diagram showing the elongation of the same polymeric mesh product after implantation.
Figure 4C:
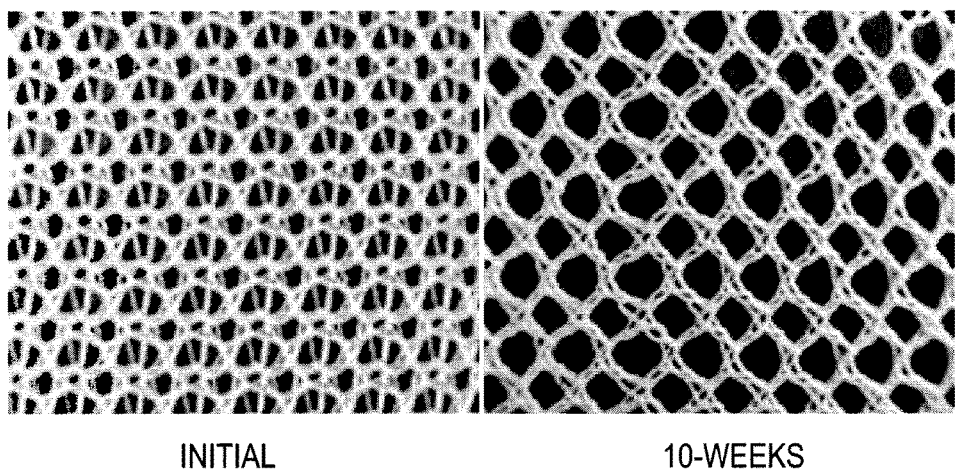
FIG. 4C shows the appearance of the same mesh product prior to implantation and 10 weeks after being exposed to conditions that simulate an in vivo environment.

As shown in FIGS. 4A and 4B, the SAM8 product has an initial stiffness and area weight comparable to current polypropylene (PP) meshes. The initial strength of the SAM8 product is almost 3 times the strength of MERSELENE® mesh (Ethicon). The elongation, however, almost doubles 8 weeks after implantation due to the degradation of the absorbable copolymer material in vivo. FIG. 4C shows the appearance of the mesh product prior to implantation and 10 weeks after being exposed to conditions that simulate the in vivo environment.

The meshes in Examples 1-4 have a total porosity within the range of 30-40% with an initial average pore size of about 1 mm and a long-term average pore size 2-3 mm following the degradation of fiber B. The meshes have thickness in the range of 0.3 to 0.5 mm (with 0.4 mm being a typical value), burst pressure in the range of 592 kPa to 1.18 MPa, initial area weight ranging from 70 to 110 g/m$^2$ (preferentially from 70 to 80 g/m$^2$) and long-term (>2-5 months) residual mass of approximately 40-70% of the initial mass). The meshes have minimum initial burst strength values of about 300 N and a long-term burst strength of at least 180 N.

Example 5: Preparation of a Typical, Selectively Absorbable, Warp-Knitted Mesh Using Multifilament Fibers of Polypropylene (PP) and Polydioxanone Fiber Preparation and Characteristics
  Fiber A—Polypropylene
  Fiber Count: 10-15
  Denier Range: 130-180 g/9000 m
  Tenacity Range: >3 g/denier
  Ultimate Elongation: >30%
  Fiber B—Polydioxanone
  Fiber Count: 5-10
  Denier Range: 150-200 g/9000 m
  Tenacity Range: >3.0 g/denier
  Ultimate Elongation: >30%

General Method for Composite Mesh Construction

Selectively absorbable mesh (SAM) is comprised of two fibers (A and B), of which fiber A is non-absorbable and fiber B is absorbable Polydioxanone. Each pattern is knit using a composite construction made from two individual patterns that coexist in one mesh. Knit constructions are produced using a two-step process of warping fiber onto beams and constructing meshes using a raschel knitting machine in the art. As indicated the knit construction is made from multifilament fiber.

Subsequent to mesh knitting, knit mesh is heat set by stretching a tubular mesh over a stainless steel circular mandrel. To accommodate heat setting of the SAM mesh on circular mandrels, the flat mesh sheet is edge sewn into a tube using a standard sewing machine and high-strength polyethylene terephthalate fiber. Heat setting was completed at 70-90° C. for 1-2 hours while under high vacuum (<1 torr). Meshes were then cut from the mandrel to produce a stabilized sheet of mesh.

Knitting Process (Mesh Patterns)

The knitting process utilizes two warped beams of fiber A threaded on bars 1 and 2 and two warped beams of fiber B threaded on bars 3 and 4. The knitting machine is a Raschel knitting machine of 18 gauge needles. Fiber B is knit in a 2 bar marquisette pattern and fiber A knit in a 2 bar sand-fly net pattern with all guide bars for each pattern threaded 1-in and 1-out.

Knitting Pattern (28 Courses Per Inch)
  Bar 1—1-0/1-2/2-3/2-1//2x (1-in, 1-out)
  Bar 2—2-3/2-1/1-0/1-2//2x (1-in, 1-out)
  Bar 3—1-0/0-1//4x (1-in, 1-out)
  Bar 4—0-0/3-3//4x (1-in, 1-out)

Typical Mechanical Properties

The resultant mechanical properties are based on the selection of Fiber B, and for this example the time at which the mesh transitions from a structurally stable/stiff construction to a more flexible/compliant construction is 1-2 months. Minimum initial burst strength values of 300 N and a long-term burst strength of at least 180 N are typical and comparable to current clinically-relevant meshes.

Example 6: Methods for Mesh Property Determination

Mesh Area Weight

The determination of mesh area weight followed option C in ASTM D3776-07 Standard test method for mass per unit area of fabric. Specifically, the area weight for each mesh construction was determined by first using a lever arm fabric cutter to cut 10 cm×15 cm rectangular samples of annealed mesh. Each sample was then weighed (Mettler Toledo, AB204-S) to the nearest one thousandth of a gram. The following equation was used to calculate the area weight in grams per square meter.

$$\text{Area Weight (g/m}^2\text{)} = \text{Weight of Samples (g)} / 0.015 \text{ (m}^2\text{)}$$

Mesh Thickness

For meshes, thickness is measured as the distance between the upper and lower surfaces of two plates compressed against the mesh and subjected to a specified pressure. Mesh thickness was determined using the procedure as outlined in the ASTM D1777-96 Standard test method for thickness of textile materials. Using a lever arm fabric cutter, random 57 mm×57 mm square samples of the annealed mesh were obtained for evaluation. Each sample was measured in the center of the mesh swatch using a comparator (B.C. Ames, 05-0191) gauge. The comparator gauge was equipped with a 28.7 mm diameter foot and used a 9 ounce weight to apply the standardized pressure to the mesh.

Mesh Porosity

Mesh porosity was characterized as (1) a percentage of the mesh covered by pores and as (2) the mean pore size. Photographic images were obtained using a microscope equipped with a camera (Cannon USA, EOS 20D) and evaluated using NIS Elements (Nikon Instruments, Inc) software. The total pore area, or open apertures, for each mesh was calculated from an obtained image that contained at least 20 large apertures. Manipulation of the images was performed by high-contrast colorizing of the pores followed by software determination of the color covered area. Using this information, the fraction of area covered by pores compared to the total area was determined as a percentage. Using the same image, individual pores were analyzed with respect to area. Since pore shapes are highly variable, both within and among different meshes, the area of individual pores were recalculated to an equivalent average pore diameter and reported as such.

Tensile Properties (Uniaxial)

Tensile strength is determined using ASTM D5035-11 Standard test method for breaking force and elongation of textile fabrics (strip method). Briefly, tensile testing of 2.5 cm wide strips of mesh samples was conducted using a universal testing machine (MTS, Synergie 100) equipped with a 500 N load cell and a set of wedge grips (Chatillon, GF-9). Each sample was tested using a gauge length of 25.4 mm and constant cross-head traverse of 2.33 mm/s.

Burst Properties (Multiaxial)

Human abdominal pressures range from 0.2 kPa (resting) to 20 kPa maximum. According to Laplace's law, a thin-walled sphere where the total vessel wall tension [(pressure× vessel radius)/2) is independent of the layer thickness (wall thickness/vessel radius <<1) can be described by, $F = p \times d/4$ (N/cm) where d=diameter, p=pressure, and F=wall tension/cm of circumference. If the longitudinal diameter of the human abdominal wall is 32 cm, a tensile force of 16 N/cm is produced at the maximum pressure.

To define the physiologic strain associated with a 16 N/cm load, Junge et al. (Junge K et al. Hernia 2001; 5(3):113-8), analyzed the abdominal wall of 14 fresh corpses and determined that longitudinally the average extension was 25%±7%. The mesh extension at 16 N/cm was calculated initially (t=0) and after in vitro conditioning using the ball burst test method according to ASTM D 3787-07 Standard test method for bursting strength of textiles-constant-rate-of-traverse ball burst test using a universal testing machine (MTS, Synergie 200) equipped with a 1 kN load cell.

For the determination, a two-step process was employed. First, the linear displacement of the ball (mm) was recorded for a predetermined resistive force (71 N). The value of 71 N is derived from the diameter of the opening within the clamp plates of the fixture, 4.44 cm×16 N/cm=71 N. Second, the radial mesh length within the circular openings of the clamp plates was determined. Initially, the mesh is constrained within the 4.44 cm diameter and is all in one plane. Tests were performed using a 2.54 cm/min constant-rate-of-traverse for the ball. Prior to the initiation of the test, a 0.1 N preload force was placed against the mesh by the ball. As the test progresses, the ball pushes the mesh downward and creates a cone like shape with the radius of the ball as the tip. A mathematical expression which relates the linear travel of the ball to the change in length of the mesh was determined. The obtained equation was used to predict the change in mesh length for relevant ball linear displacements and provided the mesh extension (%) as a function of the applied force (N).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A single-layer polymeric mesh consisting of one layer having essentially identical first and second sides, the one layer consisting of two fiber types co-knit to form single layer;
    a) wherein the first fiber type consists of an absorbable polymeric multifilament fiber, the absorbable polymeric multifilament fiber providing from 30% to 60% by weight of the single-layer polymeric mesh; and
    b) the second fiber type consists of a non-absorbable synthetic monofilament polymeric fiber, the non-absorbable synthetic monofilament polymeric fiber selected from polyethylene with a denier of 60-150 g/9000 m or polypropylene with a denier of 130-180 g/9000 m, wherein said non-absorbable synthetic monofilament polymeric fiber has an ultimate elongation of greater than 30%;
    wherein said absorbable polymeric multifilament fiber is warp knit with said non-absorbable synthetic monofilament fiber to form said single layer polymeric mesh, where the absorbable fiber is knit in a 2 bar marquisette pattern and the non-absorbable fiber is knit in a 2 bar sand-fly net pattern with all guide bars for each pattern threaded 1-in and 1-out;
    wherein said absorbable fibers are interlaced with said non-absorbable fibers and at least partly traverses the non-absorbable fibers such that the absorbable fibers restrict uniaxial and multiaxial movement by said non-absorbable fibers; and
    wherein said single layer warp-knit mesh has at least two different strength profiles including an initial stiff phase prior to degradation of the absorbable polymeric multifilament fiber and a later extensible phase that results after degradation of the absorbable polymeric multifilament fiber.

2. The single-layer polymeric mesh of claim 1, wherein the non-absorbable synthetic monofilament polymeric fiber facilitates uniaxial and multiaxial deformation subsequent to a substantial loss of mechanical properties contributed by the absorbable polymeric multifilament fiber to the single-layer polymeric mesh.

3. The single-layer polymeric mesh of claim 1, wherein said single-layer polymeric mesh provides structural stability to developing neotissue at an implantation site.

4. The single-layer polymeric mesh of claim 1, wherein said single-layer polymeric mesh has long-term force-extensional characteristics compatible with surrounding tissues at an implantation site.

5. The single-layer polymeric mesh of claim 1, wherein said absorbable polymeric multifilament fiber substantially degrades in vivo at an implantation site in a period of 1-12 weeks.

6. The single-layer polymeric mesh of claim 1, wherein said absorbable polymeric multifilament fiber comprises a polyaxial, segmented biodegradable copolyester fiber.

7. The single-layer polymeric mesh of claim 6, wherein said polyaxial, segmented biodegradable copolyester fiber comprises a glycolide/l-lactide/trimethylene carbonate copolymer.

8. The single-layer polymeric mesh of claim 1, wherein said absorbable polymeric multifilament fiber comprises a homopolymer of polydioxanone.

9. The single-layer polymeric mesh of claim 1, wherein said absorbable polymeric multifilament fiber comprises a PEG/glycolide/l-lactide copolymer fiber.

10. The single-layer polymeric mesh of claim 1, wherein said absorbable polymeric multifilament fiber has a denier range of 25-200 g/9000 m.

11. The single-layer polymeric mesh of claim 1, wherein said absorbable polymeric multifilament fiber has an ultimate elongation that is equal to or less than an ultimate elongation of said non-absorbable synthetic monofilament polymeric fiber.

12. The single-layer polymeric mesh of claim 1, wherein said single-layer polymeric mesh has an initial weight, an initial area weight ranging from about 70 to 110 g/m$^2$, and a long-term residual weight of about 40-70% of the initial weight.

13. The single-layer polymeric mesh of claim 1, wherein said single-layer polymeric mesh has a total porosity within a range of 30-40% with an initial average pore size of about 1 mm and a long-term average pore size of about 2-3 mm.

14. The single-layer polymeric mesh of claim 1, wherein the non-absorbable synthetic monofilament polymeric fiber comprises polyethylene.

15. The single-layer polymeric mesh of claim 1, wherein the non-absorbable synthetic monofilament polymeric fiber comprises polypropylene.

16. The single-layer polymeric mesh of claim 1, wherein the non-absorbable synthetic monofilament polymeric fiber has an ultimate elongation of 40-80%.

17. The single-layer polymeric mesh of claim 1, having a thickness in a range of 0.1 mm-2 mm.

* * * * *